(12) United States Patent
Iida

(10) Patent No.: US 11,634,386 B2  
(45) Date of Patent: Apr. 25, 2023

(54) METHOD FOR PRODUCING DIPHENYLSULFONE COMPOUND

(71) Applicant: KONISHI CHEMICAL IND. CO., LTD., Wakayama (JP)

(72) Inventor: Norihito Iida, Wakayama (JP)

(73) Assignee: Konishi Chemical Ind. Co. Ltd., Wakayama (JP)

( * ) Notice: Subject to any disclaimer, the term of this patent is extended or adjusted under 35 U.S.C. 154(b) by 0 days.

(21) Appl. No.: 17/596,494

(22) PCT Filed: Mar. 9, 2021

(86) PCT No.: PCT/JP2021/009124  
§ 371 (c)(1),  
(2) Date: Dec. 10, 2021

(87) PCT Pub. No.: WO2021/187215  
PCT Pub. Date: Sep. 23, 2021

(65) Prior Publication Data  
US 2022/0306572 A1  Sep. 29, 2022

(30) Foreign Application Priority Data  
Mar. 16, 2020 (JP) .............................. JP2020-045585

(51) Int. Cl.  
*C07C 315/04* (2006.01)

(52) U.S. Cl.  
CPC .................. *C07C 315/04* (2013.01)

(58) Field of Classification Search  
USPC ........................................................ 568/33  
See application file for complete search history.

(56) References Cited

U.S. PATENT DOCUMENTS

| | | | |
|---|---|---|---|
| 5,072,049 A | 12/1991 | Stumpp et al. | |
| 5,189,223 A | 2/1993 | Ogata et al. | |
| 6,348,631 B1 | 2/2002 | Desmurs et al. | |

FOREIGN PATENT DOCUMENTS

| | | | |
|---|---|---|---|
| CN | 1622935 A | 6/2005 | |
| CN | 1810782 A | 8/2006 | |
| CN | 1982293 A | 6/2007 | |
| EP | 1491528 A1 | 12/2004 | |
| JP | 48-043728 | 12/1973 | |
| JP | 57-035559 A | 2/1982 | |
| JP | 10-025277 A | 1/1998 | |
| JP | 2002-88055 A | 3/2002 | |

OTHER PUBLICATIONS

Office Action for Chinese Application No. 202180003852.4 dated Jun. 1, 2022, 5 pgs.  
Melissa Cooke et al., "Lewis acid catalysed microwave-assisted synthesis of diaryl sulfones and comparison of associated carbon dioxide emissions", Journal of Molecular Catalysis A: Chemical, 2009, 303, pp. 132-136.  
International Search Report for PCT/JP2021/009124, dated Apr. 6, 2021, 3 pgs.  
PubChem, https://pubchem.ncbi.nlm.nih.gov/#query=anisole, p. 1, (Retrieved on Jan. 20, 2023).

*Primary Examiner* — Ana Z Muresan  
(74) *Attorney, Agent, or Firm* — Preti Flaherty Beliveau & Pachios LLP

(57) ABSTRACT

A diphenylsulfone compound containing 4,4'-dihydroxydiphenylsulfone is produced in good yield in a short time and at a relatively low temperature. A diphenylsulfone compound represented by formula (2) below is produced by irradiating, with microwaves, a compound represented by formula (1) below and a sulfonating agent so that a dehydration condensation reaction is carried out.

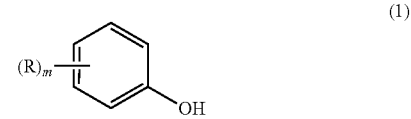

(1)

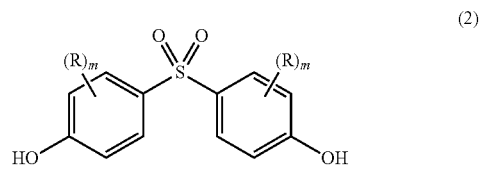

(2)

6 Claims, 1 Drawing Sheet

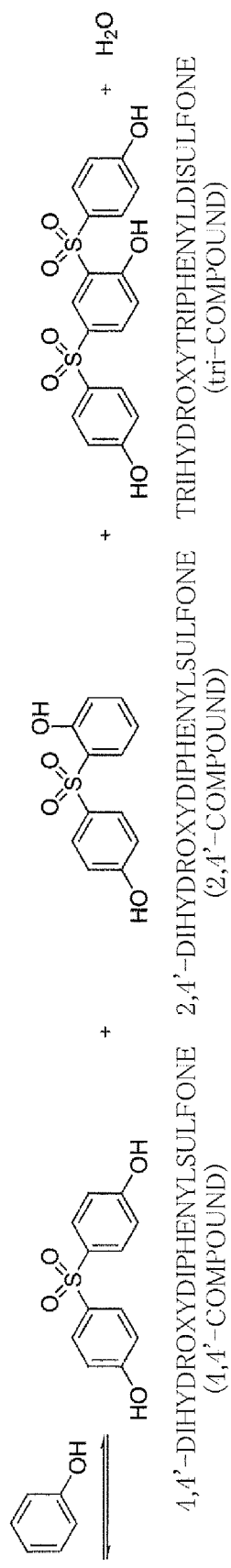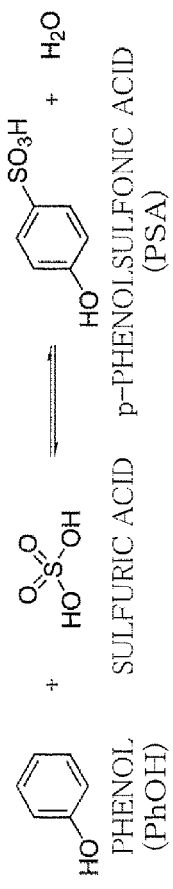

METHOD FOR PRODUCING DIPHENYLSULFONE COMPOUND

TECHNICAL FIELD

The present invention relates to a method for producing a diphenylsulfone compound.

BACKGROUND ART 4,4'-dihydroxydiphenylsulfone is a compound which has been used as a dyeing aid and a thermal paper developer for a long time. In recent years, this diphenylsulfone compound has been in increasing demand, as an alternative to bisphenol A, which is suspected to be an endocrine disruptor, or a super engineering plastic monomer.

As a conventional method for synthesizing 4,4'-dihydroxydiphenylsulfone, there is a method in which phenol and a sulfonating agent (e.g., concentrated sulfuric acid, sulfuric anhydride, fuming sulfuric acid, and chlorosulfonic acid) are heat treated at a high temperature so that the phenol and the sulfonating agent undergo dehydration condensation. However, according to this method, progress of a reaction is slow, and a high temperature and a long time are required, resulting in an increase in impurities and a decrease in yield. Therefore, various improved methods have been considered.

For example, Patent Literature 1 discloses a method for producing 4,4'-dihydroxydiphenylsulfone, in which phenol and a sulfonating agent are heat treated at a high temperature in the presence of at least one compound selected from the group consisting of zinc compounds, iron compounds, magnesium compounds, boron compounds, and phosphorus compounds.

Patent Literature 2 discloses a method for producing 4,4'-dihydroxydiphenylsulfone, in which phenol and sulfuric acid are heat treated at a high temperature in the absence of an inert solvent.

CITATION LIST

Patent Literature

[Patent Literature 1]
Japanese Patent Application Publication, Tokukaishou, No. 57-35559 (1982)
[Patent Literature 2]
Japanese Patent Application Publication Tokukaihei No. 2-235857 (1990)

SUMMARY OF INVENTION

Technical Problem

However, the conventional techniques as described above still have room for improvement in terms of a reaction temperature and a reaction time.

An object of an aspect of the present invention is to produce a diphenylsulfone compound containing 4,4'-dihydroxydiphenylsulfone, in good yield in a short time and at a relatively low temperature.

Solution to Problem

As a result of conducting diligent studies in order to attain the above object, the inventors of the present invention have found that irradiating phenols and a sulfonating agent with microwaves allows a dehydration condensation reaction to progress at a lower temperature and in a shorter time than in the conventional techniques, thereby completing the present invention.

Specifically, a method for producing a diphenylsulfone compound in accordance with an aspect of the present invention includes the following feature:

A method for producing a diphenylsulfone compound, including carrying out a dehydration condensation reaction by irradiating, with microwaves, a compound represented by formula (1) below and a sulfonating agent, to produce a diphenylsulfone compound represented by formula (2) below,

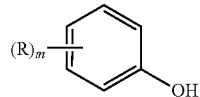
(1)

where: each R independently represents a hydrogen atom, a halogen atom, an alkyl group having 1 to 5 carbon atoms, an aryl group having 6 to 10 carbon atoms, or an aralkyl group having 7 to 10 carbon atoms; and m represents an integer of 0 to 4,

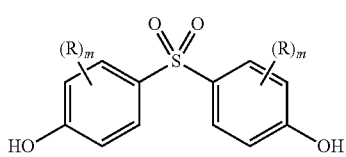
(2)

where: each R independently represents a hydrogen atom, a halogen atom, an alkyl group having 1 to 5 carbon atoms, an aryl group having 6 to 10 carbon atoms, or an aralkyl group having 7 to 10 carbon atoms; and m represents an integer of 0 to 4.

Advantageous Effects of Invention

According to an aspect of the present invention, it is possible to produce a diphenylsulfone compound containing 4,4'-dihydroxydiphenylsulfone, in good yield in a short time and at a relatively low temperature.

BRIEF DESCRIPTION OF DRAWINGS

FIG. 1 is a drawing illustrating an example of a dehydration condensation reaction.

DESCRIPTION OF EMBODIMENTS

The following description will discuss embodiments of the present invention in detail. Note, however, that the present invention is not limited to the embodiments, but can be altered within this disclosure. The present invention also encompasses, in its technical scope, any embodiment derived by combining technical means disclosed in differing embodiments. Note that the expression "A to B", representing a numerical range, herein means "not less than A but not more than B", unless otherwise specified in this specification.

In a method for producing a diphenylsulfone compound in accordance with an embodiment of the present invention, a dehydration condensation reaction is carried out by irradiating, with microwaves, a compound represented by formula (1) below and a sulfonating agent, to produce a diphenylsulfone compound represented by formula (2) below,

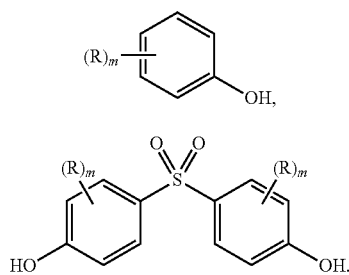

In formula (1), each R independently represents a hydrogen atom, a halogen atom, an alkyl group having 1 to 5 carbon atoms, an aryl group having 6 to 10 carbon atoms, or an aralkyl group having 7 to 10 carbon atoms.

Examples of the halogen atom include a fluorine atom, a chlorine atom, a bromine atom, and an iodine atom. Of these examples, chlorine, bromine, and iodine are preferable, and chlorine is more preferable.

The alkyl group having 1 to 5 carbon atoms may be linear or branched, and examples thereof include a methyl group, an ethyl group, an n-propyl group, an isopropyl group, an n-butyl group, an isobutyl group, a sec-butyl group, a tert-butyl group, an n-pentyl group, a 1-methylbutyl group, a 2-methylbutyl group, a 1-ethylpropyl group, and a neopentyl group. Of these examples, the methyl group, the ethyl group, the n-propyl group, the n-butyl group, and the n-pentyl group are preferable, and the methyl group and the ethyl group are more preferable.

Examples of the aryl group having 6 to 10 carbon atoms include a phenyl group, a tolyl group, a xylyl group, a mesityl group, and a naphthyl group. Of these examples, the phenyl group and the tolyl group are preferable, and the phenyl group is more preferable.

Examples of the aralkyl group having 7 to 10 carbon atoms include a benzyl group, a phenylethyl group, a phenylpropyl group, and a phenylbutyl group. Of these examples, the benzyl group, the phenylethyl group, and the phenylpropyl group are preferable, and the benzyl group and the phenylethyl group are more preferable.

$m$ is an integer of 0 to 4, preferably an integer of 0 to 3, and more preferably an integer of 0 to 2.

Examples of the compound represented by formula (1) include phenol and phenol derivatives. Specific examples of the phenol derivatives include fluorophenol, chlorophenol, bromophenol, iodophenol, methylphenol, ethylphenol, n-propylphenol, isopropylphenol, n-butylphenol, isobutylphenol, sec-butylphenol, tert-butylphenol, n-pentylphenol, 1-methylbutylphenol, 2-methylbutylphenol, 1-ethylpropylphenol, neopentylphenol, phenylphenol, tolylphenol, xylylphenol, mesitylphenol, naphthylphenol, benzylphenol, phenylethylphenol, phenylpropylphenol, and phenylbutylphenol. Of these examples, phenol, chlorophenol, bromophenol, iodophenol, methylphenol, ethylphenol, n-propylphenol, n-butylphenol, pentylphenol, phenylphenol, tolylphenol, benzylphenol, phenylethylphenol, and phenylpropylphenol are preferable, and phenol, chlorophenol, methylphenol, ethylphenol, phenylphenol, benzylphenol, and phenylethylphenol are more preferable.

Examples of the sulfonating agent, which is reacted with the compound represented by formula (1), include sulfuric acid, sulfuric anhydride, fuming sulfuric acid, chlorosulfonic acid, bis(sulfur dioxide)-1,4-diazabicyclo[2.2.2]octane adduct, sulfur dioxide 1-methylpyrrolidine adduct, disodium disulfite, and dipotassium disulfite. Of these examples, sulfuric acid, sulfuric anhydride, fuming sulfuric acid, and chlorosulfonic acid are preferable, and sulfuric acid and fuming sulfuric acid are more preferable. Each of these sulfonating agents may be used alone, or two or more of these sulfonating agents may be used at the same time.

In formula (2) above, R and m are as defined in formula (1) above.

Examples of the compound represented by formula (2) include 4,4'-dihydroxydiphenylsulfone and 4,4'-dihydroxydiphenylsulfone derivatives. Specific examples of the 4,4'-dihydroxydiphenylsulfone derivatives include difluoro-4,4'-dihydroxydiphenylsulfone, dichloro-4,4'-dihydroxydiphenylsulfone, dibromo-4,4'-dihydroxydiphenylsulfone, diiodo-4,4'-dihydroxydiphenylsulfone, dimethyl dihydroxydiphenylsulfone, diethyl-4,4'-dihydroxydiphenylsulfone, di-n-propyl-4,4'-dihydroxydiphenylsulfone, diisopropyl-4,4'-dihydroxydiphenylsulfone, di-n-butyl-4,4'-dihydroxydiphenylsulfone, diisobutyl-4,4'-dihydroxydiphenylsulfone, di-sec-butyl-4,4'-dihydroxydiphenylsulfone, di-tert-butyl-4,4'-dihydroxydiphenylsulfone, di-n-pentyl-4,4'-dihydroxydiphenylsulfone, di-1-methylbutyl-4,4'-dihydroxydiphenylsulfone, di-2-methylbutyl-4,4'-dihydroxydiphenylsulfone, di-1-ethylpropyl-4,4'-dihydroxydiphenylsulfone, dineopentyl-4,4'-dihydroxydiphenylsulfone, diphenyl-4,4'-dihydroxydiphenylsulfone, ditolyl-4,4'-dihydroxydiphenylsulfone, dixylyl-4,4'-dihydroxydiphenylsulfone, dimesityl-4,4'-dihydroxydiphenylsulfone, dinaphthyl-4,4'-dihydroxydiphenylsulfone, dibenzyl-4,4'-dihydroxydiphenylsulfone, diphenylethyl-4,4'-dihydroxydiphenylsulfone, diphenylpropyl-4,4'-dihydroxydiphenylsulfone, and diphenylbutyl-4,4'-dihydroxydiphenylsulfone.

In the dehydration condensation reaction, the compound represented by formula (1) is used in an amount of, but is not limited to, preferably not less than 2.0 mol with respect to 1.0 mol of the sulfonating agent. Further, the compound represented by formula (1) is used in an amount of preferably not more than 3.0 mol, more preferably not more than 2.5 mol, and still more preferably not more than 2.2 mol, with respect to 1.0 mol of the sulfonating agent. The compound represented by formula (1) is used in an amount of preferably not less than 2.0 mol but not more than 3.0 mol with respect to 1.0 mol of the sulfonating agent, because the sulfonating agent and the compound represented by formula (1) in a reaction system are consumed in a balanced manner, thus a compound which remains unreacted is small in amount, and consequently the yield of the diphenylsulfone compound is improved.

By irradiating, with microwaves, the compound represented by formula (1) and the sulfonating agent, the dehydration condensation reaction progresses.

FIG. 1 is a drawing illustrating an example of the dehydration condensation reaction. As shown in FIG. 1, the compound represented by formula (1) and the sulfonating agent (phenol and sulfuric acid in FIG. 1) undergo a dehydration reaction, so that a phenylsulfone compound (p-phenolsulfonic acid (PSA) in FIG. 1) and water are produced. Subsequently, the phenylsulfone compound and the compound represented by formula (1) undergo a condensation reaction, so that the diphenylsulfone compound which is represented by formula (2) and which is a 4,4'-compound (compound having hydroxy groups at 4- and 4'-positions) (4,4'-dihydroxydiphenylsulfone in FIG. 1), a 2,4'-compound (compound having hydroxy groups at 2- and 4'-positions) which is an isomer (2,4'-dihydroxydiphenylsulfone in FIG. 1), a tri-compound (compound having three hydroxy groups) which is a by-product (trihydroxytriphenyldisulfone in FIG. 1), and water are produced.

The above reaction system has some viscosity at an ordinary temperature. Therefore, in a case where the dehydration condensation reaction is caused to progress by conventional heating through heat transfer, e.g., by heating with use of an oil bath or a heater, it is difficult to uniform a temperature in the system even in a case where mixing is carried out. Therefore, in a vicinity of a wall surface of a reaction vessel, the reaction progresses at a high temperature, whereas the temperature in a central portion of the reaction vessel remains low and the reaction does not progress easily. In a case where the heating is continued until the temperature in the central portion of the reaction vessel reaches a sufficient temperature, a by-product tends to be produced in a large amount in the vicinity of the wall surface of the reaction vessel because the reaction progresses at a high temperature for a long time in the vicinity of the wall surface of the reaction vessel.

In contrast, irradiation with microwaves makes it possible to efficiently heat the entire reaction system in a short time as compared with the conventional heating through heat transfer, so that unevenness in heating is less likely to occur. In particular, water generated in the dehydration condensation reaction between the compound represented by formula (1) and the sulfonating agent preferentially absorbs the microwaves, and thus quickly vaporizes. Therefore, by removing, from a liquid phase, the water which has vaporized, it is possible to advance the dehydration condensation reaction. Consequently, it is possible to cause the reaction to progress at a favorable reaction rate without the need to heat the reaction system to around the boiling point of the compound represented by formula (1). This makes it possible to obtain a desired yield of the diphenylsulfone compound at a relatively low temperature and in a short time, and also makes it possible to suppress production of a by-product.

In the method for producing a diphenylsulfone compound in accordance with an embodiment of the present invention, the reaction system is heated so that the temperature of the reaction system in the dehydration condensation reaction is preferably not lower than 115° C. and more preferably not lower than 125° C. and thereby the reaction progresses at a favorable rate. Further, the temperature of the reaction system in the dehydration condensation reaction is preferably not higher than 190° C. and more preferably not higher than 180° C. so that production of a by-product is suppressed.

After the temperature of the reaction system is raised, the temperature of the reaction system is preferably kept in the above preferable temperature range for a certain period of time. This keeping time can be set as appropriate, depending on the scale etc. of the reaction system, but is set to, for example, preferably not shorter than 120 minutes and more preferably not shorter than 200 minutes so that the yield is increased. Further, the keeping time is preferably not longer than 700 minutes and more preferably not longer than 670 minutes so that production of a by-product is suppressed and productivity is increased.

The frequency of the microwaves is not limited to any particular one, and may be any frequency of 300 MHz to 300 GHz. For example, the frequency may be 2.45 GHz, 5.8 GHz, 24 GHz, 915 MHz, 896 MHz, or 434 MHz. Further, microwaves of a single frequency may be emitted, or microwaves of a plurality of frequencies may be emitted. In a case where microwaves of a plurality of frequencies are emitted, the microwaves of the plurality of frequencies may be emitted at different times, or may be emitted at the same time. The microwaves may be emitted in a single mode or in a multimode.

The output of the microwaves is not limited to any particular one, provided that the temperature of the reaction system can quickly reach the above preferable temperature range and the reaction system can maintain the temperature. After the temperature of the reaction system is raised, a method of emitting the microwaves and the output of the microwaves may be changed as appropriate so that the temperature is kept within a desired temperature range. For example, the microwaves may be emitted continuously or intermittently. Further, the output of the microwaves may be changed, depending on a desired rate of temperature rise.

In order that the uniformity of the temperature of the reaction system is increased, the dehydration condensation reaction is preferably carried out while the compound represented by formula (1) and the sulfonating agent are mixed. This makes it possible to further increase the uniformity of the temperature of the reaction system and also increase an opportunity of contact of the compound represented by formula (1) with the sulfonating agent, thereby increasing the reaction rate.

In the method for producing a diphenylsulfone compound in accordance with an embodiment of the present invention, it is possible to further increase the reaction rate by carrying out the dehydration condensation reaction in the presence of a boron compound.

Examples of the boron compound which is suitably used in an embodiment of the present invention include: boric acid; borate salts such as sodium borate, ammonium borate, calcium borate, magnesium borate, sodium tetraborate, potassium tetraborate, lithium tetraborate, ammonium tetraborate, lithium tetraborate, sodium metaborate, calcium metaborate, lithium metaborate, potassium metaborate, and borax; boron oxides; and borohydride salts such as sodium borohydride, lithium borohydride, and potassium borohydride. Of these examples, boric acid and boron oxides are preferable, and boric acid is more preferable. Each of these boron compounds may be used alone, or two or more of these boron compounds may be used at the same time.

In order that the effect of improving the reaction rate is sufficiently brought about, the boron compound is used in an amount of preferably not less than 0.001 mol, and more preferably not less than 0.005 mol, with respect to 1.0 mol of the sulfonating agent. Further, the boron compound is used in an amount of preferably not more than 0.5 mol, and more preferably not more than 0.1 mol, with respect to 1.0 mol of the sulfonating agent, otherwise the effect of improving the reaction rate is less likely to be brought about due to a decomposition reaction of the boron compound itself.

In the conventional methods disclosed in Patent Literatures 1 and 2, an excessive amount of phenol substantially serves as a reaction solvent. Therefore, in these methods, in order to reliably cause a reaction to progress, it is necessary to heat a reaction system to a temperature around or equal to or higher than the boiling point (about 182° C.) of phenol. However, even in a case where the reaction is carried out at such a high temperature, a reaction rate is slow, and therefore it takes a long time to achieve a desired yield. Therefore, there is a problem that, by carrying out the reaction at a high temperature for a long time, a by-product is increased and a yield is lowered.

In contrast, according to an embodiment of the present invention, the dehydration condensation reaction is carried out in the presence of a solvent which is not reactive with a raw material compound and a product. Therefore, it is possible to promote vaporization of water generated by the dehydration reaction and further increase the reaction rate, without the need to heat the reaction system to a temperature as high as that in the conventional method.

Furthermore, the presence of the solvent in the reaction system facilitates controlling the temperature of the reaction system to fall within a preferable range. Moreover, the presence of the solvent in the reaction system facilitates separating and reusing the raw material compound and the product in the reaction system.

The solvent which is suitably used in an embodiment of the present invention include nonpolar solvents having no functional group that is reactive with the compound represented by formula (1), the compound represented by formula (2), and the sulfonating agent in the reaction system. The solvent preferably has a boiling point falling within a preferable temperature range of the dehydration condensation reaction.

Examples of such a solvent include: aromatic hydrocarbon solvents such as toluene, o-xylene, m-xylene, p-xylene, and mesitylene; aromatic halogenated hydrocarbon solvents such as chlorobenzene, o-dichlorobenzene, m-dichlorobenzene, p-dichlorobenzene, bromobenzene, and iodobenzene; and aliphatic and alicyclic hydrocarbon solvents such as octane, nonane, decane, ethylcyclohexane, n-propylcyclohexane, isopropylcyclohexane, butylcyclohexane, isobutylcyclohexane, and tert-butylcyclohexane.

In order that the vaporization of water is promoted and the effect of improving the reaction rate is sufficiently brought about, the solvent is used in an amount of preferably not less than 1.0 part by mass, and more preferably not less than 1.2 parts by mass, with respect to 1 part by mass of the sulfonating agent. Further, in order that the productivity is increased, the solvent is used in an amount of preferably not more than 2.5 parts by mass, and more preferably not more than 2.4 parts by mass, with respect to 1 part by mass of the sulfonating agent.

In a particularly preferable embodiment, the dehydration condensation reaction is preferably carried out in the presence of the solvent and the boron compound. This makes it possible to cause the temperature of the reaction system to be lower, and also makes it possible to further increase the reaction rate.

The present invention is not limited to the embodiments, but can be altered by a skilled person in the art within the scope of the claims. The present invention also encompasses, in its technical scope, any embodiment derived by combining technical means disclosed in differing embodiments.

Specifically, a method for producing a diphenylsulfone compound in accordance with an aspect of the present invention includes the following features:

[1] A method for producing a diphenylsulfone compound, including carrying out a dehydration condensation reaction by irradiating, with microwaves, a compound represented by formula (1) below and a sulfonating agent, to produce a diphenylsulfone compound represented by formula (2) below,

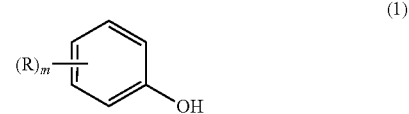

where: each R independently represents a hydrogen atom, a halogen atom, an alkyl group having 1 to 5 carbon atoms, an aryl group having 6 to 10 carbon atoms, or an aralkyl group having 7 to 10 carbon atoms; and m represents an integer of 0 to 4,

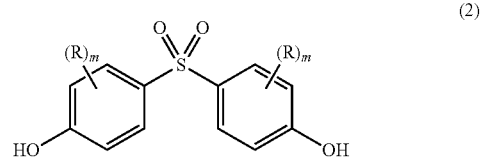

where: each R independently represents a hydrogen atom, a halogen atom, an alkyl group having 1 to 5 carbon atoms, an aryl group having 6 to 10 carbon atoms, or an aralkyl group having 7 to 10 carbon atoms; and m represents an integer of 0 to 4;

[2] The method as described in [1], wherein the dehydration condensation reaction is carried out in the presence of a solvent;

[3] The method as described in [2], wherein the solvent is used in an amount of 1.0 part by mass to 2.5 parts by mass with respect to 1 part by mass of the sulfonating agent;

[4] The method as described in any one of [1] through [3], wherein the compound represented by formula (1) is used in an amount of 2.0 mol to 3.0 mol with respect to 1.0 mol of the sulfonating agent;

[5] The method as described in any one of [1] through [4], wherein the dehydration condensation reaction is carried out in the presence of a boron compound; and

[6] The method as described in [5], wherein the boron compound is used in an amount of 0.001 mol to 0.5 mol with respect to 1.0 mol of the sulfonating agent.

EXAMPLES

The present invention will be described in more detail with reference to Examples. However, the scope of the present invention is not limited by these Examples. Note that "%" in Examples means "% by mass", unless otherwise specified.

Example 1

As a reaction vessel, a 500-mL four-neck flask equipped with a stirring device, a Dean-Stark tube, and a condenser tube was prepared.

Into the reaction vessel, 58.3 g (0.62 mol) of phenol, 51.9 g of mesitylene, and 30.6 g (0.31 mol) of 98% sulfuric acid were introduced. While this reaction system was stirred at a stirring speed of 250 rpm, the reaction system was heated by irradiating the reaction system with microwaves (frequency: 2.45 GHz, output: 230 W, multimode), until a temperature inside the reaction system became 150° C. After the temperature inside the reaction system reached 150° C., the temperature inside the reaction system was kept in a range of 150° C. to 164° C. and reflux was carried out for 5 hours and 40 minutes, while dehydration was carried out with use of the Dean-Stark tube. As a result, a crude product was obtained.

The resulting crude product was analyzed with use of a high-performance liquid chromatograph (HPLC) (NexeraXR, manufactured by SHIMADZU CORPORATION) under the following analysis conditions.

[Analysis Conditions]
Column: YMC-Pack ODS-A (5 μm, 6.0 mmφ×30 cm; manufactured of YMC CO., LTD.)
Column temperature: 40° C.
Mobile phase: acetonitrile/0.05 M potassium dihydrogen phosphate buffer solution=30/70 (v/v)
Flow rate: 1.0 mL/min
Detection wavelength: 225 nm As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=87.4/8.4/2.1/1.8/0.2. The yield of 4,4'-dihydroxydiphenylsulfone with respect to the amount of the sulfuric acid used (vs.-sulfuric acid yield) was 76.8%. Reaction conditions are shown in Table 1 below. Results are shown in Table 2 below.

Example 2

In a manner similar to that in Example 1, 58.3 g (0.62 mol) of phenol, 66.6 g of chlorobenzene, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 200 W, multimode), until a temperature inside the reaction system became 128° C. After the temperature inside the reaction system reached 128° C., the temperature inside the reaction system was kept in a range of 128° C. to 132° C. and reflux was carried out for 10 hours and 30 minutes, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=63.6/20.7/0.7/9.7/5.4. The yield of 4,4'-dihydroxydiphenylsulfone with respect to the amount of the sulfuric acid used (vs.-sulfuric acid yield) was 63.2%. Reaction conditions are shown in Table 1 below. Results are shown in Table 2 below.

Example 3

In a manner similar to that in Example 1, 58.3 g (0.62 mol) of phenol, 43.8 g of decane, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 230 W, multimode), until a temperature inside the reaction system became 147° C. After the temperature inside the reaction system reached 147° C., the temperature inside the reaction system was kept in a range of 147° C. to 174° C. and reflux was carried out for 6 hours, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=81.9/7.6/6.0/2.6/1.9. The yield of 4,4'-dihydroxydiphenylsulfone with respect to the amount of the sulfuric acid used (vs.-sulfuric acid yield) was 75.8%. Reaction conditions are shown in Table 1 below. Results are shown in Table 2 below.

Example 4

In a manner similar to that in Example 1, 58.3 g (0.62 mol) of phenol, 51.9 g of mesitylene, 1.0 g (0.02 mol) of boric acid, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 230 W, multimode), until a temperature inside the reaction system became 150° C. After the temperature inside the reaction system reached 150° C., the temperature inside the reaction system was kept in a range of 150° C. to 164° C. and reflux was carried out for 5 hours, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=91.4/4.6/1.6/0.5/1.9. The yield of 4,4'-dihydroxydiphenylsulfone with respect to the amount of the sulfuric acid used (vs.-sulfuric acid yield) was 87.6%. Reaction conditions are shown in Table 1 below. Results are shown in Table 2 below.

Example 5

In a manner similar to that in Example 1, 58.3 g (0.62 mol) of phenol, 51.9 g of mesitylene, 0.2 g (0.0032 mol) of boric acid, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 230 W, multimode), until a temperature inside the reaction system became 150° C. After the temperature inside the reaction system reached 150° C., the temperature inside the reaction system was kept in a range of 150° C. to 164° C. and reflux was carried out for 5 hours and 10 minutes, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=92.5/4.1/1.9/0.8/0.8. The yield of 4,4'-dihydroxydiphenylsulfone with respect to the amount of the sulfuric acid used (vs.-sulfuric acid yield) was 91.4%. Reaction conditions are shown in Table 1 below. Results are shown in Table 2 below.

Example 6

In a manner similar to that in Example 1, 58.3 g (0.62 mol) of phenol, 66.6 g of chlorobenzene, 1.0 g (0.02 mol) of boric acid, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 200 W, multimode), until a temperature inside the reaction system became 128° C. After the temperature inside the reaction system reached 128° C., the temperature inside the reaction system was kept in a range of 128° C. to 132° C. and reflux was carried out for 7 hours and 30 minutes, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=87.4/9.1/1.6/0.2/1.7. The yield of 4,4'-dihydroxydiphenylsulfone with respect to the amount of the sulfuric acid used (vs.-sulfuric acid yield) was 83.4%. Reaction conditions are shown in Table 1 below. Results are shown in Table 2 below.

Example 7

In a manner similar to that in Example 1, 58.3 g (0.62 mol) of phenol, 43.8 g of decane, 1.0 g (0.02 mol) of boric acid, and 30.6 g (0.31 mol) of 98% sulfuric acid were introduced into a reaction vessel. While this reaction system was stirred at a stirring speed of 250 rpm, the reaction system was heated by irradiating the reaction system with microwaves (frequency: 2.45 GHz, output: 230 W, multimode), until a temperature inside the reaction system became 147° C. After the temperature inside the reaction system reached 147° C., the temperature inside the reaction system was kept in a range of 147° C. to 174° C. and reflux was carried out for 6 hours, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=88.5/3.5/6.5/1.3/0.1. The yield of 4,4'-dihydroxydiphenylsulfone with respect to the amount of the sulfuric acid used (vs.-sulfuric acid yield) was 77.4%. Reaction conditions are shown in Table 1 below. Results are shown in Table 2 below.

Comparative Example 1

Into a reaction vessel similar to that in Example 1, 58.3 g (0.62 mol) of phenol, 51.9 g of mesitylene, and 30.6 g (0.31 mol) of 98% sulfuric acid were introduced. While this reaction system was stirred at a stirring speed of 250 rpm, the reaction system was heated in an oil bath at 180° C., until a temperature of a central portion of the reaction vessel became 150° C. After the temperature reached 150° C., the temperature was kept in a range of 150° C. to 164° C. and reflux was carried out for 5 hours and 40 minutes, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=67.8/13.8/1.4/11.5/5.5. The yield of 4,4'-dihydroxydiphenylsulfone with respect to the amount of the sulfuric acid used (vs.-sulfuric acid yield) was 67.6%. Reaction conditions are shown in Table 1 below. Results are shown in Table 2 below.

Comparative Example 2

Into a reaction vessel similar to that in Example 1, 58.3 g (0.62 mol) of phenol, 66.6 g of chlorobenzene, and 30.6 g (0.31 mol) of 98% sulfuric acid were introduced. While this reaction system was stirred at a stirring speed of 250 rpm, the reaction system was heated in an oil bath at 170° C., until a temperature of a central portion of the reaction vessel became 128° C. After the temperature reached 128° C., the temperature was kept in a range of 128° C. to 132° C. and reflux was carried out for 10 hours and 30 minutes, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=52.8/23.5/0.5/16.3/7.0. The yield of 4,4'-dihydroxydiphenylsulfone with respect to the amount of the sulfuric acid used (vs.-sulfuric acid yield) was 55.9%. Reaction conditions are shown in Table 1 below. Results are shown in Table 2 below.

Comparative Example 3

Into a reaction vessel similar to that in Example 1, 58.3 g (0.62 mol) of phenol, 43.8 g of decane, and 30.6 g (0.31 mol) of 98% sulfuric acid were introduced. While this reaction system was stirred at a stirring speed of 250 rpm, the reaction system was heated in an oil bath at 190° C., until a temperature of a central portion of the reaction vessel became 147° C. After the temperature reached 147° C., the temperature was kept in a range of 147° C. to 174° C. and reflux was carried out for 6 hours, while dehydration was carried out with use of a Dean-Stark tube. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=79.5/7.6/3.0/8.5/1.5. The yield of 4,4'-dihydroxydiphenylsulfone with respect to the amount of the sulfuric acid used (vs.-sulfuric acid yield) was 71.5%. Reaction conditions are shown in Table 1 below. Results are shown in Table 2 below.

Comparative Example 4

As a reaction vessel, a 500-mL four-neck flask equipped with a stirring device and a condenser tube was prepared.

Into the reaction vessel, 58.3 g (0.62 mol) of phenol, 51.9 g of mesitylene, and 30.6 g (0.31 mol) of 98% sulfuric acid were introduced. While this reaction system was stirred at a stirring speed of 250 rpm, the reaction system was heated by irradiating the reaction system with microwaves (frequency: 2.45 GHz, output: 230 W, multimode), until a temperature inside the reaction system became 150° C. After the temperature inside the reaction system reached 150° C., reflux was carried out for 5 hours and 40 minutes, without dehydration. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=5.8/3.7/1.3/69.8/19.3. The yield of 4,4'-dihydroxydiphenylsulfone with respect to the amount of the sulfuric acid used (vs.-sulfuric acid yield) was 4.8%. Reaction conditions are shown in Table 1 below. Results are shown in Table 2 below.

Comparative Example 5

Into a reaction vessel similar to that in Comparative Example 4, 58.3 g (0.62 mol) of phenol, 66.6 g of chlorobenzene, and 30.6 g (0.31 mol) of 98% sulfuric acid were introduced. While this reaction system was stirred at a stirring speed of 250 rpm, the reaction system was heated by irradiating the reaction system with microwaves (frequency: 2.45 GHz, output: 200 W, multimode), until a temperature inside the reaction system became 128° C. After the temperature inside the reaction system reached 128° C., reflux was carried out for 10 hours and 30 minutes, without dehydration. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=3.8/2.4/0.1/74.7/19.0. The yield of 4,4'-dihydroxydiphenylsulfone with respect to the amount of the sulfuric acid used (vs.-sulfuric acid yield) was 3.1%. Reaction conditions are shown in Table 1 below. Results are shown in Table 2 below.

Comparative Example 6

Into a reaction vessel similar to that in Comparative Example 4, 58.3 g (0.62 mol) of phenol, 43.8 g of decane, and 30.6 g (0.31 mol) of 98% sulfuric acid were introduced. While this reaction system was stirred at a stirring speed of 250 rpm, the reaction system was heated by irradiating the reaction system with microwaves (frequency: 2.45 GHz, output: 230 W, multimode), until a temperature inside the reaction system became 147° C. After the temperature inside the reaction system reached 147° C., reflux was carried out for 6 hours, without dehydration. As a result, a crude product was obtained.

The resulting crude product was analyzed with use of an HPLC in a manner similar to that in Example 1. As a result of an analysis, detected were 4,4'-dihydroxydiphenylsulfone (4,4'-compound) as a product, 2,4'-dihydroxydiphenylsulfone (2,4'-compound) as an isomer, trihydroxytriphenyldisulfone (tri-compound) as a by-product, p-phenolsulfonic acid (PSA), and phenol (PhOH) as an unreacted compound. A mass ratio between these compounds was 4,4'-compound/2,4'-compound/tri-compound/PSA/PhOH=10.0/5.5/0.05/57.8/26.5. The yield of 4,4'-dihydroxydiphenylsulfone with respect to the amount of the sulfuric acid used (vs.-sulfuric acid yield) was 10.0%. Reaction conditions are shown in Table 1 below. Results are shown in Table 2 below.

TABLE 1

| | Solvent | Boric acid [mol %] | Heating means | Dehydration | Reaction time |
|---|---|---|---|---|---|
| Example 1 | Mesitylene | No | Microwaves (230 W) | Yes | 5 hours and 40 minutes |
| Example 2 | Chlorobenzene | No | Microwaves (200 W) | Yes | 10 hours and 30 minutes |
| Example 3 | Decane | No | Microwaves (230 W) | Yes | 6 hours |
| Example 4 | Mesitylene | 5 | Microwaves (230 W) | Yes | 5 hours |
| Example 5 | Mesitylene | 1 | Microwaves (230 W) | Yes | 5 hours and 10 minutes |
| Example 6 | Chloro- | 5 | Microwaves | Yes | 7 hours and |

TABLE 1-continued

|  | Solvent | Boric acid [mol %] | Heating means | Dehydration | Reaction time |
|---|---|---|---|---|---|
| Example 7 | benzene Decane | 5 | (200 W) Microwaves (230 W) | Yes | 30 minutes 6 hours |
| Comparative Example 1 | Mesitylene | No | Oil bath (180° C.) | Yes | 5 hours and 40 minutes |
| Comparative Example 2 | Chlorobenzene | No | Oil bath (170° C.) | Yes | 10 hours and 30 minutes |
| Comparative Example 3 | Decane | No | Oil bath (190° C.) | Yes | 6 hours |
| Comparative Example 4 | Mesitylene | No | Microwaves (230 W) | No | 5 hours and 40 minutes |
| Comparative Example 5 | Chlorobenzene | No | Microwaves (200 W) | No | 10 hours and 30 minutes |
| Comparative Example 6 | Decane | No | Microwaves (230 W) | No | 6 hours |

TABLE 2

|  | 4,4'-compound [% by mass] | 2,4'-compound [% by mass] | Tri-compound [% by mass] | PSA [% by mass] | PhOH [% by mass] | Yield of 4,4'-compound [%] |
|---|---|---|---|---|---|---|
| Example 1 | 87.4 | 8.4 | 2.1 | 1.8 | 0.2 | 76.8 |
| Example 2 | 63.6 | 20.7 | 0.7 | 9.7 | 5.4 | 63.2 |
| Example 3 | 81.9 | 7.6 | 6.0 | 2.6 | 1.9 | 75.8 |
| Example 4 | 91.4 | 4.6 | 1.6 | 0.5 | 1.9 | 87.6 |
| Example 5 | 92.5 | 4.1 | 1.9 | 0.8 | 0.8 | 91.4 |
| Example 6 | 87.4 | 9.1 | 1.6 | 0.2 | 1.7 | 83.4 |
| Example 7 | 88.5 | 3.5 | 6.5 | 1.3 | 0.1 | 77.4 |
| Comparative Example 1 | 67.8 | 13.8 | 1.4 | 11.5 | 5.5 | 67.6 |
| Comparative Example 2 | 52.8 | 23.5 | 0.5 | 16.3 | 7.0 | 55.9 |
| Comparative Example 3 | 79.5 | 7.6 | 3.0 | 8.5 | 1.5 | 71.5 |
| Comparative Example 4 | 5.8 | 3.7 | 1.3 | 69.8 | 19.3 | 4.8 |
| Comparative Example 5 | 3.8 | 2.4 | 0.1 | 74.7 | 19.0 | 3.1 |
| Comparative Example 6 | 10.0 | 5.5 | 0.05 | 57.8 | 26.5 | 10.0 |

From a comparison between Example 1 and Comparative Example 1 in each of which mesitylene was used as a solvent, it was shown that use of microwaves as a heating means allowed an increase in reaction rate of a dehydration condensation reaction and allowed an improvement in yield of a 4,4'-compound in the same reaction time, as compared with a case where an oil bath was used. Similar results were obtained from a comparison between Example 2 and Comparative Example 2 in each of which chlorobenzene was used as a solvent and from a comparison between Example 3 and Comparative Example 3 in each of which decane was as a solvent.

From a comparison between Example 1 and Examples 4 and 5 in each of which mesitylene as a solvent, it was shown that use of boric acid allowed a further increase in reaction rate and allowed obtainment of a 4,4'-compound in high yield in a short reaction time. Similar results were obtained from a comparison between Example 2 and Example 6 in each of which chlorobenzene was used as a solvent. Also from a comparison between Example 3 and Example 7 in each of which decane was used as a solvent, it was shown that use of boric acid allowed obtainment of a 4,4'-compound in high yield.

From the results of Example 5, it was shown that even in a case where boric acid was used in an amount of only 1 mol % with respect to sulfuric acid, a favorable catalytic effect was obtained.

From a comparison between Example 1 and Comparative Example 4, it was found that in a case where water produced by a reaction was not removed, a reaction rate of a dehydration condensation reaction was remarkably decreased and the yield of a 4,4'-compound was remarkably decreased. Similar results were obtained from a comparison between Example 2 and Comparative Example 5 in each of which chlorobenzene was used as a solvent and from a comparison between Example 3 and Comparative Example 6 in each of which decane was used as a solvent.

INDUSTRIAL APPLICABILITY

The present invention can be suitably used for manufacture of a diphenylsulfone compound which can be used in various applications including, but not limited to, materials such as a dyeing aid and a thermal paper developer, alternatives to bisphenol A, super engineering plastic monomers, and the like.

The invention claimed is:

1. A method for producing a diphenylsulfone compound, comprising carrying out a dehydration condensation reaction while removing water generated from the dehydration condensation reaction by irradiating, with microwaves, a compound represented by formula (1) below and a sulfonating agent, to produce a diphenylsulfone compound represented by formula (2) below,

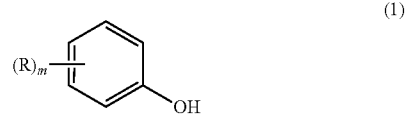

(1)

where: each R independently represents a hydrogen atom, or an alkyl group having 1 to 5 carbon atoms; and m represents an integer of 0 to 4,

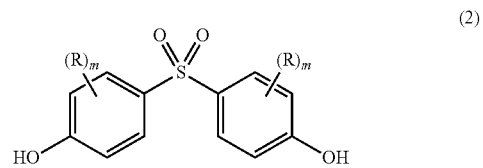

(2)

where: each R independently represents a hydrogen atom, or an alkyl group having 1 to 5 carbon atoms; and m represents an integer of 0 to 4;
wherein the dehydration condensation reaction is carried out in the presence of a solvent which is not reactive with the compound represented by formula 1, the sulfonating agent, and the diphenylsulfone compound represented by formula 2; and
wherein the temperature of the reaction system in the dehydration condensation reaction is not lower than 115° C. and not higher than 174° C.

2. The method as set forth in claim 1, wherein the solvent is used in an amount of 1.0 part by mass to 2.5 parts by mass with respect to 1 part by mass of the sulfonating agent.

3. The method as set forth in claim 1, wherein the compound represented by formula (1) is used in an amount of 2.0 mol to 3.0 mol with respect to 1.0 mol of the sulfonating agent.

4. The method as set forth in claim 1, wherein the dehydration condensation reaction is carried out in the presence of a boron compound.

5. The method as set forth in claim 4, wherein the boron compound is used in an amount of 0.001 mol to 0.5 mol with respect to 1.0 mol of the sulfonating agent.

6. The method of claim 1, wherein the frequency of the microwaves is in a range of 300 MHZ to 300 GHz.

* * * * *